United States Patent
Shaw et al.

(10) Patent No.: US 8,240,480 B2
(45) Date of Patent: Aug. 14, 2012

(54) SORTING MINED MATERIAL

(75) Inventors: Raymond Walter Shaw, Princes Hill (AU); Barry Lavin, Churchlands (AU)

(73) Assignee: Technological Resources Pty. Limited, Melbourne, Victoria (AU)

( * ) Notice: Subject to any disclaimer, the term of this patent is extended or adjusted under 35 U.S.C. 154(b) by 0 days.

(21) Appl. No.: 12/445,832

(22) PCT Filed: Oct. 16, 2007

(86) PCT No.: PCT/AU2007/001567
§ 371 (c)(1),
(2), (4) Date: Dec. 29, 2009

(87) PCT Pub. No.: WO2008/046136
PCT Pub. Date: Apr. 24, 2008

(65) Prior Publication Data
US 2010/0206778 A1    Aug. 19, 2010

(30) Foreign Application Priority Data

Oct. 16, 2006    (AU) .................................. 2006905746

(51) Int. Cl.
*B03B 9/00*    (2006.01)
(52) U.S. Cl. ................ 209/11; 209/3; 209/567; 423/22; 75/10.67; 75/416; 75/571; 75/628
(58) Field of Classification Search .............. 209/3, 587; 75/406; 73/571
See application file for complete search history.

(56) References Cited

U.S. PATENT DOCUMENTS

| | | | | |
|---|---|---|---|---|
| 3,337,328 | A | * | 8/1967 | Lawver ........................ 75/10.67 |
| 4,177,064 | A | * | 12/1979 | Wanzenberg et al. .......... 75/416 |
| 4,236,640 | A | | 12/1980 | Knight |
| 5,170,666 | A | | 12/1992 | Larsen |
| 5,985,221 | A | * | 11/1999 | Knecht ........................... 423/22 |
| 6,112,903 | A | * | 9/2000 | Kimmel et al. ................. 209/11 |
| 2001/0054331 | A1 | * | 12/2001 | Yasuda et al. .................. 75/628 |
| 2008/0257793 | A1 | * | 10/2008 | Valerio .......................... 209/567 |
| 2010/0206778 | A1 | * | 8/2010 | Shaw et al. ...................... 209/3 |

FOREIGN PATENT DOCUMENTS

| | | |
|---|---|---|
| GB | 2057123 A | 3/1981 |
| GB | 2188727 A | 10/1987 |
| WO | 03102250 A1 | 12/2003 |
| WO | 2006034553 A1 | 4/2006 |

OTHER PUBLICATIONS

Nagaraj, D.R., Minerals Recovery and Processing, Kirk-Othmer Encyclopedia of Chemical Technology, 2005, sec. 1.5, pp. 9-13 (see my note), v. 16, John Wiley & Sons, Inc.

* cited by examiner

*Primary Examiner* — Terrell Matthews
(74) *Attorney, Agent, or Firm* — The Webb Law Firm

(57) ABSTRACT

A method of sorting mined material for subsequent processing to recover valuable material, such as valuable metals, from the mined material is disclosed. The method includes a combination of selective breakage of mined material, for example, by using microwaves and/or high pressure grinding rolls, subsequent size separation, and then particle sorting of a coarse fraction of the separated material based on differential heating and thermal imaging.

20 Claims, 3 Drawing Sheets

Version with microwave breakage and thermal image based sorting of both coarse and fines Version with microwave breakage and thermal image based sorting of coarse only

SORTING MINED MATERIAL

BACKGROUND OF THE INVENTION

1. Field of the Invention

The present invention relates to a method and an apparatus for sorting mined material for subsequent processing to recover valuable material, such as valuable metals, from the mined material.

The present invention also relates to a method and an apparatus for recovering valuable material, such as valuable metals, from mined material.

2. Description of the Related Art

The mined material may be any mined material that contains valuable material, such as valuable metals.

Typically, the mined material includes mined ores that include minerals that contain valuable metals, such as copper and nickel, in sulphide and/or oxide forms.

SUMMARY OF THE INVENTION

The present invention is based on a realisation that the use of a combination of selective breakage of mined material (for example, by using microwaves and/or high pressure grinding rolls), subsequent size separation, and then particle sorting of a coarse fraction of the separated material based on differential heating and thermal imaging is an effective combination of steps for separating particles that contain valuable material from relatively barren particles with respect to the valuable material.

The present invention is concerned particularly with rejecting low grade mined material, which tends to be in coarse material rather than fines, before it enters a more expensive downstream processing step or steps, such as fine grinding, flotation, leaching, or smelting steps. Rejecting low grade mined material reduces the amount of mined material to be treated and consequently the cost of the further processing in existing plants. Consequently, rejecting low grade mined material opens up opportunities to reduce processing costs per unit valuable material recovered and to free up capacity for more mined material to be processed in plants. In some instances the present invention may also be used to make a product for direct sale rather than for further processing, which is a considerable advantage.

Ore sorting is currently being used for mined material. However, current sorting methods suffer from difficulties in detecting valuable material in mined material. Combining ore sorting with selective breakage of mined material is advantageous because it allows low grade or barren material in mined material to be identified and at least some of the low grade or barren material to be separated using simple sorting apparatus such as screens or the like. Consequently, more complex sorting apparatus, such as apparatus using air to remove individual particles, is only required to treat a smaller fraction of the mined material.

According to the present invention there is provided a method of sorting mined material, such as mined ore, for subsequent processing to recover valuable material, such as valuable metals, from the mined material that includes the steps of:

(a) breaking particles of mined material and separating the particles into at least a coarse fraction and a fines fraction on the basis of particle size;

(b) subjecting the coarse fraction of the particles from step (a) to some form of heating and subsequent thermal imaging analysis and identifying particles that contain valuable material; and (c) separating the coarse fraction into (i) particles that contain valuable material on the basis of thermal imaging analysis and (ii) particles that are relatively barren with respect to the valuable material.

The amount of the coarse fraction that is processed in step (b) and the amounts of that coarse fraction that are separated for further downstream recovery of valuable material and for disposal as waste will depend in any situation on the type of mined ore and the valuable material of interest and the available downstream recovery processing options and the costs of those options. Typically, the amount of material that is identified as a waste by-product that is not processed in downstream recovery processing options is at least 10%, more preferably at least 20%, of the mined material. Removing this amount of material from downstream processing is a significant advantage.

Typically, the fines fraction of the particles from step (a) is processed further to recover valuable material from the fines.

The terms "coarse" and "fine" are used herein as relative terms that describe that one fraction has larger particle sizes than another fraction. The actual particle sizes that are regarded as "coarse" and "fine" are dependent on the context, i.e. the type of mined material, against which the terms are used.

Typically, the valuable particles from step (c) are processed further to recover valuable material from the particles.

Typically, the remaining particles from step (c) are a waste by-product.

The method may include a step of further breaking the valuable particles from step (c).

Typically, a fines fraction from the further breaking step described in the preceding paragraph is processed further to recover valuable material from the fines. Typically, a coarse fraction from the further breaking step in the preceding paragraph is a waste by-product.

The method may include the steps of subjecting the fines fraction of the particles from step (a) to thermal imaging analysis and identifying particles that contain valuable material and separating the fines fraction into (i) particles that contain valuable material on the basis of thermal imaging analysis and (ii) particles that are relatively barren with respect to the valuable material.

Typically the valuable particles are processed further to recover valuable material from the particles.

Typically, the remaining particles are a waste by-product.

The further processing of the valuable particles may be any suitable step or steps including, by way of example only, heap leaching, pressure oxidation leaching, and smelting steps.

Preferably the basis of thermal imaging analysis is that particles that contain higher levels of valuable material will respond differently to at least one heating method than the more barren particles to an extent that the difference can be detected for example using one of the commonly available thermal imaging systems based on infrared detectors. These thermal imaging systems are commonly used in areas such as monitoring body temperature for possible SARS, examining electrical connections such as in substations, and monitoring tanks and pipes and now have sufficient accuracy to detect small (i.e. <2° C.) temperature differences.

Preferably step (b) includes heating particles in the coarse fraction by exposing the particles to microwaves, particularly in situations where the valuable material and other material in mined materials have different susceptibilities to the microwave energy and therefore heat differentially. Most commonly the valuable materials will be much more susceptible than the other material present and therefore the particles with higher levels of these valuable materials will become hotter than the more barren particles. In any given situation, the selection of the wavelength or other characteristics of the microwave energy will be on the basis of facilitating a different thermal response of the valuable materials from the other materials. Different water contents, and therefore different extents of heating, of the valuable materials and the other mined materials is one other possible basis for selecting the microwave energy characteristics. Also, the amounts and/or the distribution of microwave susceptible minerals, such as sulphides, in the mined materials are another possible basis for this selection.

Step (a) may be any suitable option or combination of options for breaking mined material into the coarse fraction and the fines fraction.

One example of a suitable option for step (a) is to use high pressure grinding rolls.

Preferably step (a) includes using microwave energy to break particles in the mined material into the coarse fraction and the fines fraction.

The term "microwave energy" is understood herein to mean electromagnetic radiation that has frequencies in the range of 0.3-300 GHz.

Preferably step (a) includes using pulsed microwave energy to break particles in the mined material.

More preferably step (a) includes using pulsed high energy microwave energy to break particles in the mined material.

The term "high energy" is understood herein to mean values substantially above those within conventional household microwaves, i.e. substantially above 1 kW.

Preferably the energy of the microwave energy is at least 20 kW.

More preferably the energy of the microwave energy is at least 50 kW.

More preferably step (a) includes using pulsed high energy microwave energy to break particles in the mined material and to heat particles in at least the coarse fraction to a suitable temperature for thermal image analysis in step (b).

The use of microwave energy in step (a) may be as described in International publication numbers WO 03/102250 and WO 06/034553 in the name of the applicant and the disclosure in the International publications is incorporated herein by cross-reference.

The use of pulsed microwave energy minimises the power requirements of the method and maximises thermal cycling of the ore particles.

Preferably the pulsed microwave energy includes pulses of short duration.

The term "short duration" is understood herein to mean that the time period of each pulse is less than 1 second.

Preferably the pulse time period is less than 0.1 second.

The pulse time period may be less than 0.01 second.

More preferably the pulse time period is less than 0.001 second.

The time period between pulses of microwave energy may be set as required depending on a number of factors.

Preferably the time period between pulses is 10-20 times the pulse time period.

The particles may be exposed to one or more pulses of microwaves to achieve the desired level of micro-cracking for step (a) and heating for step (b). This can be achieved in a single installation which releases microwave energy in pulses. This can also be achieved in an installation having multiple exposure points at spaced intervals along a path of movement of the mined material, with each of the exposure points releasing its own characteristic microwave energy in pulses or continuously. In some situations the particles may be exposed to microwave energy having characteristics selected for heating the particles and separately exposed to microwave energy having characteristics selected for breaking up the particles. For example, microwave energy for heating particles may be of lower energy and be either pulsed or continuous unlike that used to achieve fragmentation of the particles.

The wavelength of the microwave energy and the exposure time may be selected depending on relevant factors.

Relevant factors may include ore type, particle size, particle size distribution, and requirements for subsequent processing of the ore.

The method includes any suitable steps for exposing mined ore to microwave energy.

One suitable option includes allowing mined ore to free-fall down a transfer chute past a microwave energy generator, such as described in International publication number WO 03/102250.

The free-fall option is one preferred option in a mining industry environment because of the materials handling issues that are often associated with the mining industry.

Because the level of heating is small, another option is to pass the ore through a microwave cavity on a moving bed, preferably a mixed moving bed, with a microwave generator positioned to expose ore to microwave energy such as described in International publication number WO 06/034553.

The term "moving mixed bed" is understood to mean a bed that mixes ore particles as the particles move through a microwave exposure zone or zones and thereby changes positions of particles with respect to other particles and to the incident microwave energy as the particles move through the zone or zones.

Preferably the method includes a step of crushing mined material into a manageable particle size distribution prior to step (a).

Typically, the manageable particle size distribution is one with particles having a major dimension of less than 100 mm.

Preferably the mined material is in the form of ores in which the valuable material in the form of metal that is present as a sulphide.

The applicant is interested particularly in copper-containing ores in which the copper is present as a sulphide.

The applicant is also interested in nickel-containing ores in which the nickel is present as a sulphide.

The applicant is also interested in uranium-containing ores.

The applicant is also interested in ores containing iron minerals where some of the iron minerals have disproportionately higher levels of unwanted impurities.

The applicant is also interested in diamond ores where the ore has a mix of diamond containing minerals and diamond barren minerals such as quartz.

Preferably the particles of the mined material have a major dimension of 15 cm or less prior to exposure to microwave energy in step (a).

According to the present invention there is provided a method for recovering valuable material, such as valuable metals, from mined material, such as mined ore, that includes sorting mined material according to the method described above and thereafter processing the fines fraction from step (a) and/or other particles containing valuable material and recovering valuable material.

DETAILED DESCRIPTION OF THE PREFERRED EMBODIMENTS

Figure 1:
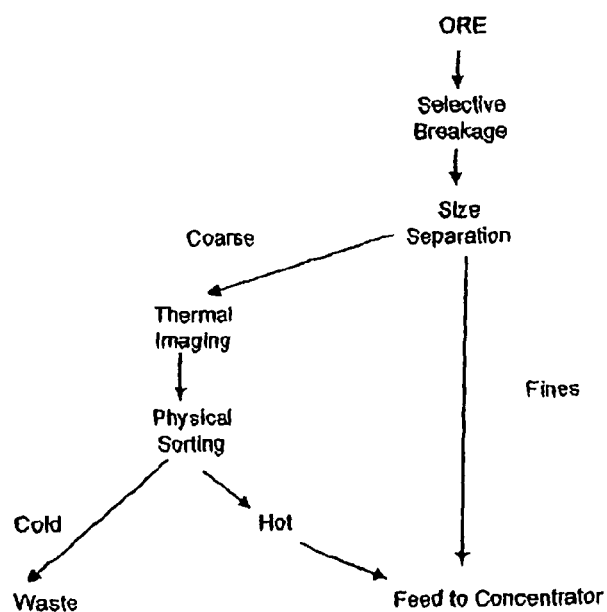
FIG. 1 is a flowsheet of one embodiment of the sorting method in accordance with the present invention.

The flow sheet of FIG. 1 is described in the context of a method of recovering a valuable component in the form of copper from copper-containing ores. It is noted that the present invention is not confined to these ores and to copper as the valuable material to be recovered.

With reference to the flow sheet of FIG. 1, feed material in the form of ore particles that have been crushed by a primary crusher to a particle size of 10-15 cm, typically less than 10 cm is subjected to selective breakage by being treated with pulsed high energy microwave energy.

Specifically, the crushed ore is supplied via a conveyor (not shown—or other suitable transfer means) to a microwave energy treatment station (not shown) and is allowed to free fall past a microwave energy generator (not shown) that exposes the ore particles to high energy pulses of microwave energy.

In an alternative embodiment, although not the only possible other embodiment, the crushed ore is supplied to an apparatus (not shown) for moving a moving mixed bed of the crushed ore past an exposure zone for microwaves produced in a microwave energy generator (not shown). For example, the moving mixed bed apparatus may be in the form of a screw feed apparatus.

The microwave energy causes localised heating of the susceptor components of the ore, which typically includes copper-containing minerals, in the ore and the differences in thermal expansion of the constituents of the ore produces regions of high stress/strain within the ore particles and causes micro-cracks to form in the particles, particularly particles containing susceptor components. Invariably, the micro-cracks lead to break down of the particles to smaller particles.

Significantly, the smaller particles tend to contain a higher percentage of copper-containing minerals.

The operating conditions, such as energy level, pulse duration, and exposure length are selected to ensure that the localised heating is sufficient to give controlled breakage of the ore particles without significantly altering the overall composition. The amount of breakage will depend largely upon how the material is to be further processed but typically, with an input feed of 10-15 cm particles, the majority of the output will have a particle size from 1-15 cm, with a substantial proportion of the output being larger than 5 cm.

The resultant stream of microwave-treated particles is separated in accordance with particle size into a coarse fraction and a fines fraction.

The fines fraction, which tends to contain more chalcopyrite or chalcocite than the coarse fraction for the reason discussed above, is supplied to a concentrator and thereafter processed to recover copper from the particles or to another suitable processing option for recovering copper.

The coarse fraction is subjected to thermal image analysis to identify particles that contain copper-containing minerals.

The basis of thermal imaging analysis insofar as the present invention is concerned is that particles that contain higher levels of valuable material will become hotter than more barren particles.

Advantageously, upstream processing conditions are selected so that the particles have sufficient retained heat for thermal image analysis without additional heating of the particles being required. If additional heating is required, it can be provided by any suitable means.

Once identified by thermal image analysis, the hotter particles are separated from the colder particles and are supplied to the concentrator mentioned above and are thereafter processed to recover copper from the particles.

The colder particles become a by-product waste and are disposed of in a suitable manner.

In general terms, the main aspects of the above-described sorting method of FIG. 1 are:

(a) microwaves break the feed material selectively, with the rocks having susceptible minerals being most prone to break due to the differential heating—for copper sulphide ores (and nickel sulphide ores and diamond ores)—and such rocks having susceptible minerals usually being a higher grade material and therefore a more valuable component;

(b) size sorting the broken material into a coarse fraction and a fines fraction provides an opportunity to reject some material in the coarse fraction, with the finer fraction generally being richer in the valuable component and being transferred for further processing to the valuable component;

(c) the more valuable particles in the coarse fraction after microwave exposure can be physically sorted further—the grades can be "measured" using thermal imaging—with the particles having higher levels of the valuable component such as copper getting hotter than the barren particles (with respect to the valuable material) and providing an opportunity to separate the coarse fraction into a more valuable fraction and a less valuable fraction; and (d) the method being particularly suited for ores which have a heterogeneous distribution of valuable material such as vein-type sulphides commonly found in copper porphyry and nickel sulphides.

Figure 2:
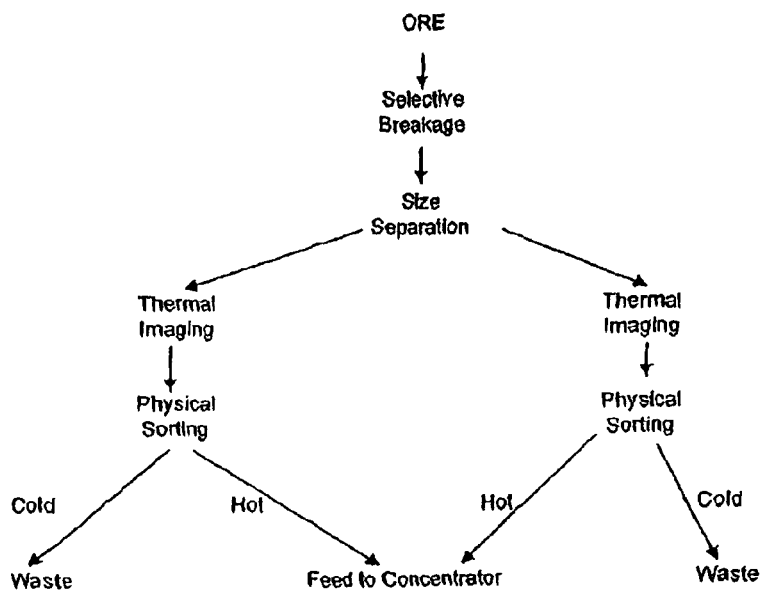
FIG. 2 is a flowsheet of another embodiment of the sorting method in accordance with the present invention.

The flow sheet of FIG. 2 is an extension of the FIG. 1 flow sheet.

Specifically, the fines fraction from the microwave treatment step is subjected to thermal image analysis in the same way as the coarse fraction.

Once identified by thermal image analysis, the hotter particles are separated from the colder particles and are supplied to the concentrator mentioned above and are thereafter processed to recover copper from the particles.

Figure 3:
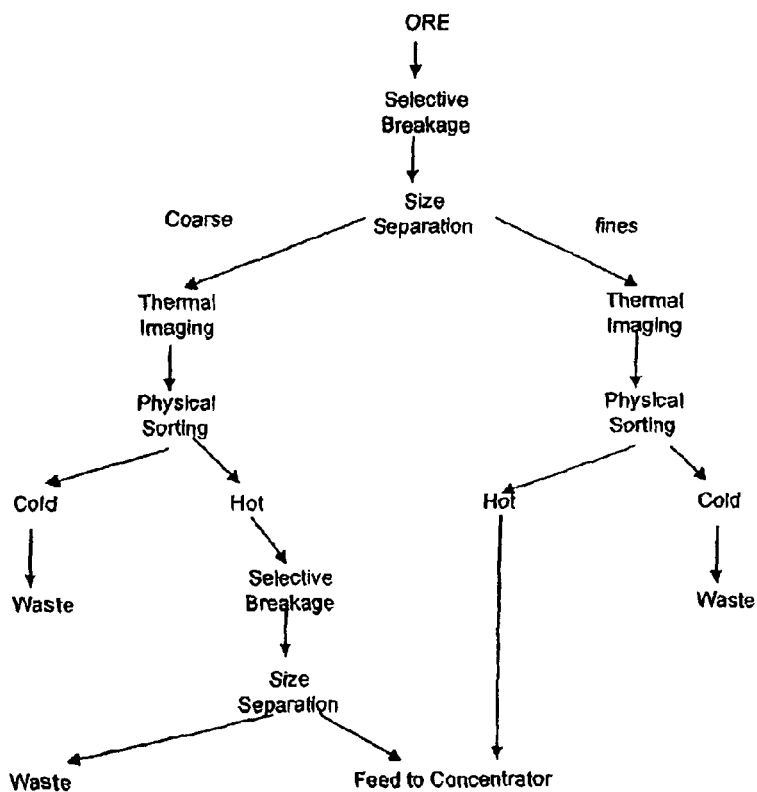
FIG. 3 is a flow sheet of another, although not the only other possible, embodiment of the sorting method in accordance with the present invention.

The flow sheet of FIG. 3 is an extension of the FIG. 2 flow sheet.

Specifically, the hotter particles from the coarse fraction are subjected to a further microwave treatment step and the treated particles are thereafter separated into a fines fraction and a coarse fraction.

The fines fraction is supplied to the concentrator mentioned above and the particles in this fraction are thereafter processed to recover copper from the particles.

The coarse fraction becomes a by-product waste and is disposed of in a suitable manner.

Many modifications may be made to the embodiments of the present invention described above without departing from the spirit and scope of the present invention.

By way of example, the present invention is not confined to the use of microwaves to selectively break mined material. High pressure grinding rolls are another option.

Moreover, the present invention extends to arrangements in which, for example, high pressure grinding rolls are used as the means for breaking mined material initially and microwaves are used to further break the coarse fraction formed in this initial step.

By way of specific example, in an alternative flow sheet (not shown) the breakage is carried out using mechanical crushing, such as with high pressure grinding rolls, and then the particles are subjected to microwave exposure primarily to give differential heating such that higher copper-containing particles (for example) can be distinguished from the more barren particles and this difference is used to enable separation.

In this alternative flow sheet the microwave application can be quite separate from the crushing and may use lower energy and/or continuous application rather than the high energy pulses needed to break the particles.

The preferred method for heating the ore to enable thermal imaging is to use microwaves to take advantage of their ability to selectively heat certain components. However, the present invention is not limited to the use of microwaves and other means may be used to give temperature differences between the mineral components.

The most preferable of these other means is to use the different response of minerals to heat through different thermal conductivity whereby selected particles within a mix heat up and cool down at different rates to others enabling them to be distinguished and separated, and through particles with higher water contents not heating as much as others due to the volatilisation of the water absorbing heat and keeping the particle temperature lower than those particles which do not lose water.

Where these properties are being utilised, conventional heating systems such as exposure to hot gas, radiant heating from a heat source and/or direct contact with a hot surface can all potentially be used.

The invention claimed is:

1. A method of sorting mined material in the form of ore particles that contain copper-containing minerals and have different grades of copper in the particles for subsequent processing to recover copper from the mined material, comprising:
   (a) breaking particles of mined material and separating the particles into at least a coarse fraction and a fines fraction on the basis of particle size, with the coarse fraction being lower grade material than the fines fraction;
   (b) subjecting the coarse fraction of the particles from step (a) to heating and subsequent thermal imaging analysis and identifying particles that contain copper on the basis of thermal imaging analysis, with hotter particles being higher grade material than colder particles; and
   (c) separating the coarse fraction into (i) particles that contain copper on the basis of thermal imaging analysis and are higher grade material, and (ii) particles that are relatively barren with respect to copper.

2. The method of claim 1, further comprising processing the particles that contain copper from step (c) to recover copper from the particles.

3. The method of claim 1, further comprising processing the fines fraction of the particles from step (a) to recover copper from the fines.

4. The method of claim 1, further comprising further breaking the particles that contain copper from step (c).

5. The method of claim 1, further comprising subjecting the fines fraction of the particles from step (a) to thermal imaging analysis and identifying particles that contain copper, and separating the fines fraction into (i) particles that contain copper on the basis of thermal imaging analysis and (ii) particles that are relatively barren with respect to copper.

6. The method of claim 5, further comprising processing the particles that contain copper further to recover valuable copper from the particles.

7. The method of claim 1, wherein step (b) includes exposing particles in the coarse fraction to microwaves in order to heat the particles.

8. The method of claim 1, wherein step (a) includes using microwave energy to break particles in the mined material into the coarse fraction and the fines fraction.

9. The method of claim 8, wherein step (a) includes using pulsed microwave energy to break particles in the mined material.

10. The method of claim 8, wherein step (a) includes using pulsed high energy microwave energy to break particles in the mined material.

11. The method of claim 9, wherein the energy of the microwave energy is at least 20 kW.

12. The method of claim 9, wherein step (a) includes using pulsed high energy microwave energy to break particles in the mined material and to heat particles in at least the coarse fraction to a suitable temperature for thermal image analysis in step (b).

13. The method of claim 9, wherein the pulsed microwave energy includes pulses of less than 0.1 second.

14. The method of claim 13, wherein the pulse time period is less than 0.01 second.

15. The method of claim 9, wherein the time period between pulses is about 10 to about 20 times the pulse time period.

16. The method of claim 1, further comprising crushing mined material into a particle size distribution of particles having a major dimension of less than 100 mm particle size distribution prior to step (a).

17. The method of claim 1, wherein the mined material is in the form of ores in which the copper is present as a sulphide.

18. A method for recovering valuable material, from mined material, comprising sorting mined material according to the method of claim 1, and thereafter, processing the fines fraction from step (a) and/or other particles containing copper and recovering copper.

19. The method of claim 7, wherein the copper and other material in mined materials have different susceptibilities to the microwave energy and therefore heat differentially.

20. The method of claim 1, wherein the mined material comprises ore.

* * * * *

UNITED STATES PATENT AND TRADEMARK OFFICE
CERTIFICATE OF CORRECTION

PATENT NO. : 8,240,480 B2  
APPLICATION NO. : 12/445832  
DATED : August 14, 2012  
INVENTOR(S) : Raymond Walter Shaw et al.

Page 1 of 1

It is certified that error appears in the above-identified patent and that said Letters Patent is hereby corrected as shown below:

Column 8, Line 12, Claim 6, after "recover" delete "valuable"

Signed and Sealed this
Thirteenth Day of November, 2012

David J. Kappos
*Director of the United States Patent and Trademark Office*